United States Patent [19]

Wheeler

[11] Patent Number: 4,632,698

[45] Date of Patent: Dec. 30, 1986

[54] BIOCIDAL 2-ARYL-1,3-CYCLOPENTANEDIONE ENOL ESTER COMPOUNDS

[75] Inventor: Thomas N. Wheeler, Charleston, W. Va.

[73] Assignee: Union Carbide Corporation, Danbury, Conn.

[21] Appl. No.: 766,782

[22] Filed: Aug. 19, 1985

Related U.S. Application Data

[60] Division of Ser. No. 528,936, Sep. 2, 1983, Pat. No. 4,551,547, which is a continuation of Ser. No. 205,650, Nov. 10, 1980, abandoned, which is a continuation-in-part of Ser. No. 944,996, Sep. 22, 1978, abandoned.

[51] Int. Cl.$^4$ .................... A01N 37/02; A01N 37/10
[52] U.S. Cl. .................................. 71/106; 71/107; 514/532; 514/546
[58] Field of Search .................. 71/106, 107; 514/546, 514/532

[56] References Cited

U.S. PATENT DOCUMENTS

| | | | |
|---|---|---|---|
| 2,841,485 | 7/1958 | Johnson et al. | 71/2.3 |
| 2,864,680 | 12/1958 | Degginger | 71/2.3 |
| 3,102,133 | 8/1963 | Chinn | 560/255 |
| 3,159,649 | 12/1964 | Brown et al. | 560/255 |
| 3,352,662 | 1/1967 | Klopping et al. | 71/88 |
| 3,476,546 | 11/1969 | Roberts et al. | 71/88 |
| 3,784,605 | 1/1974 | Durden et al. | 260/590 |
| 3,801,630 | 4/1974 | Diehl et al. | 260/551 S |
| 3,803,240 | 4/1974 | Durden et al. | 260/590 |
| 3,852,359 | 12/1974 | Dunbar et al. | 260/590 |
| 3,879,468 | 4/1975 | Durden et al. | 260/590 |
| 3,920,725 | 11/1975 | Buckle et al. | 260/468 G |
| 3,954,998 | 5/1976 | Durden et al. | 424/331 |
| 4,041,049 | 8/1977 | Muller et al. | 260/343.5 |
| 4,104,043 | 8/1978 | Durden et al. | 71/107 |

OTHER PUBLICATIONS

J. A. Durden, Jr., Biocidal Activity of Indandiones-1,3 and Related Compounds, Medical Chemistry IV, Proceeding of the 4th International Symposium on Medicinal Chemistry, Noordwijkerbout, Netherlands, Sep. 9–13, 1974, pp. 143–171.

Gren et al "2-Phenyl-4,5,6,7-Tetrahydro Etc." (1961) CA 56 P2391 (1962).

Gren et al "Intra and Intermolecular Etc." (1975) CA 83, No. 113469s also Index (1972–1976), col. 3.

*Primary Examiner*—Catherine L. Mills
*Attorney, Agent, or Firm*—Gerald L. Coon

[57] ABSTRACT

2-Aryl-1,3-cyclopentanedione enol ester compounds exhibit outstanding acaricidal and herbicidal activity.

14 Claims, No Drawings

BIOCIDAL 2-ARYL-1,3-CYCLOPENTANEDIONE ENOL ESTER COMPOUNDS

This is a division of prior U.S. application Ser. No. 528,936, filed Sept. 2, 1983, now U.S. Pat. No. 4,551,547, which is a continuation of application Ser. No. 205,650, filed Nov. 10, 1980, now abandoned, which is a continuation-in-part of application Ser. No. 944,996 filed Sept. 22, 1978, abandoned.

This invention relates to biocidal 2-aryl-1,3-cyclopentanedione enol ester compounds and methods of preparing them. In another aspect, this invention is directed to herbicidal and acaricidal compositions comprising a herbicidally or acaricidally effective amount of a compound of the instant invention. This invention is also directed to methods of controlling acarids and plant pests by subjecting them to a herbicidally or acaricidally effective amount of a compound of this invention.

More particularly, this invention relates to compounds of the formula:

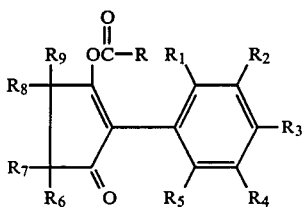

wherein:
R is hydrogen, halogen, alkyl, alkenyl, alkynyl, bicycloalkyl, bicycloalkenyl, cycloalkyl, cycloalkenyl, haloalkyl, phenyl, phenylalkyl, naphthyl or napththylalkyl all of which except hydrogen and halogen may be substituted with one or more alkyl, cyano, nitro, alkoxy, aryloxy, halogen, haloalkyl, alkoxyalkyl, alkylthio, arylthio, alkylsulfinyl, arylsulfinyl, alkylsulfonyl, arylsulfonyl, alkylsulfinylalkyl, alkylsulfonylalkyl, alkylthioalkyl or dialkylamino substituent;

$R_1$ is an alkyl, haloalkyl, halogen or polyhaloalkyl group;

$R_2$, $R_3$, $R_4$ and $R_5$ are individually hydrogen, nitro, polyhaloalkyl, halogen, cyano, alkyl, alkoxy, alkylthio, alkylsulfinyl, alkylsulfonyl, alkanoyl, amido, amino or haloalkyl group;

$R_6$, $R_7$, $R_8$ and $R_9$ are individually hydrogen, or either substituted or unsubstituted alkyl, alkenyl, cycloalkyl, cycloalkenyl or phenyl wherein the permissible substituents are one or more alkyl, alkanoyl, cycloalkyl, cycloalkenyl, cyano, halogen, nitro, alkoxy, aryloxy, alkylthio, arylthio, alkylsulfinyl, alkylsulfonyl, acylamido or dialkylamino substituents; or any two $R_6$, $R_7$, $R_8$ or $R_9$ substituents taken together are an alkylene or alkenylene chain having from 2 to 20 carbon atoms completing a 3, 4, 5, 6 or 7 membered carbon ring;

with the proviso that $R_1$, $R_2$, $R_3$, $R_4$, $R_5$, $R_6$, $R_7$, $R_8$ and $R_9$ substituents individually may not include more than ten aliphatic carbon atoms, and R may not include more than thirty aliphatic carbon atoms, and that an alkenylene chain formed by any two of $R_6$, $R_7$, $R_8$ or $R_9$ resulting in a six membered fused polycyclic ring structure may not have more than one double bond.

It is understood that the ring structures formed from $R_6$, $R_7$, $R_8$ and $R_9$ taken together may be polycyclic in nature which include those of the fused and spiro variety.

As used within this specification the prefix "aryl" designates any organic radical derived from an aromatic hydrocarbon by the removal of one hydrogen atom. Preferably, aryl designates a phenyl or naphthyl moiety.

PREFERRED EMBODIMENT OF THE INVENTION

All compounds within the purview of the above generic formula exhibit acaricidal and herbicidal activity to a greater or lesser extent. Some of these compounds exhibit very powerful acaricidal or herbicidal activity in extremely small dosages while others require larger dosages to be pesticidally effective. In general, the compounds of this invention that exhibit the highest order of herbicidal activity also exhibit the highest order of acaricidal activity. The compounds of the instant invention are particularly effective against mites, both in the egg stage and the adult stage. Acaricidal and herbicidal activity is greatest in those compounds having an alkyl or halogen group at one ortho position of the 2-phenyl moiety and a hydrogen, alkyl, alkoxy, cyano, trihalomethyl or halogen substituent at either the para position or the other ortho position of the phenyl moiety. Especially active compounds are those in which the ortho substituents are relatively small groups, such as methoxy, ethoxy, methyl, ethyl, hydrogen or halogen.

It has also been found that some of the pesticidal compositions of this invention exhibit excellent fumigant properties. Fumigant activity is defined as the ability of a pesticide to exert its pesticidal activity on an untreated surface or plant from a treated surface or plant in close proximity to the untreated area. It is believed that this property is caused, at least in part, by the low vapor pressure of the compounds allowing them to volatilize from a treated surface thereby exerting their pesticidal effects on nearby untreated areas. In addition, these compounds are relatively non-toxic to mammals when used in amounts sufficient to kill acarids or undesirable plant growth.

Preferred because of their higher level of acaricidal and herbicidal activity are the 2-aryl-1,3-cyclopentanedione enol ester compounds of this invention in which the substituents are defined as follows:

R is an alkyl group having from 1 to 30 carbon atoms, preferably from 1 to 18 carbon atoms; the preferred alkyls due to lower phytotoxicity are branched alkyls;

$R_1$ is an alkyl or halogen;

$R_2$, $R_3$, $R_4$ and $R_5$ are individually alkyl, cyano, hydrogen, alkoxy, halogen or trihalomethyl;

$R_6$ and $R_8$ are hydrogen; and $R_7$ and $R_9$ are individually hydrogen or alkyl, particularly $C_1$–$C_4$, most particularly methyl; or $R_7$ and $R_9$ taken together are an alkylene group containing four carbons completing a 6 membered fused polycyclic ring structure.

The most active and particularly preferred compounds are those in which:

R is a $C_1$–$C_{30}$ alkyl, preferably a $C_1$–$C_{18}$ alkyl group, the preferred alkyls again are branched alkyls;

$R_1$ is a methyl or halogen, particularly chlorine;

$R_2$, $R_4$ and $R_5$ are hydrogen;

$R_3$ is a methyl or chlorine;

$R_6$ and $R_8$ are hydrogen; and $R_7$ and $R_9$ taken together are an alkylene group containing four carbons completing a 6 membered fused polycyclic ring structure.

The 2-aryl-1,3-cyclopentanedione enol ester compounds of this invention can be conveniently prepared by a variety of methods. The preferred method which utilizes the 2-aryl-1,3-cyclopentanedione parent compound as the precursor is illustrated by the general reaction scheme set forth below in which R, $R_1$, $R_2$, $R_3$, $R_4$, $R_5$, $R_7$, $R_8$ and $R_9$ are as described above and X is halogen, hydroxyl, or

except as noted.

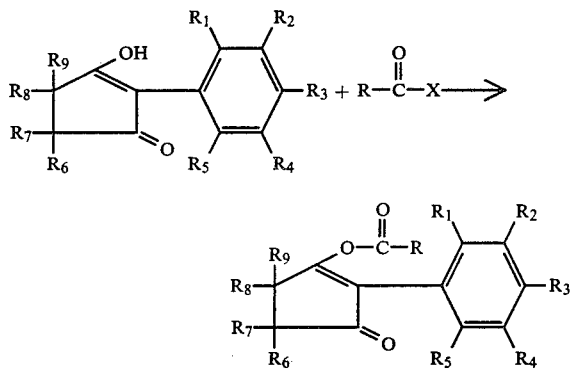

In this reaction scheme one equivalent of the corresponding 2-aryl-1,3-cyclopentanedione compound is reacted with an appropriately substituted acid, acid halide, or acid anhydride compound in the presence of at least one equivalent of an acid acceptor, preferably in an inert solvent.

The acid acceptor utilized in this reaction scheme can be either an organic or inorganic base. Illustrative of organic bases that are useful as acid acceptors are tertiary amines, such as triethylamine, pyridine, trimethylamine or 1,4-diazobicyclo[2.2.2]octane; or alkali metal alkoxides, as, for example, sodium ethoxide; potassium hydroxide and sodium hydroxide are illustrative of inorganic bases that are useful as acid acceptors. Preferred acid acceptors are triethylamine, pyridine or trimethylamine.

In general, any organic solvent that is inert to the reactants or reaction conditions may be employed in the reaction scheme shown above. Illustrative of organic solvents which are generally suitable for use in the conduct of these reactions are saturated, unsaturated and aromatic hydrocarbons, e.g. hexane, cyclohexane, octane, cyclohexane, dodecane, naphtha, decalin, kerosene, cycloheptane, benzene, toluene, xylene, napthalene or the like; ethers such as dioxane, tetrahydrofuran, diethyl ether, tetrahydropyran, 1,2-dimethoxybenzene, 1,2-diethylbenzene, the dialkyl ethers of ethylene glycol, of propylene glycol or chlorinated aliphatic hydrocarbons as, for example, chloroform, dichloromethane, 1,1-dichloroethane, carbon tetrachloride, or the like.

The reactions illustrated by the general scheme given above may also be conducted in a solvent which functions as an acid acceptor. Illustrative of such multifunctional solvents are N,N,-dimethylaniline, pyridine, α-picoline, any lutidine, collodine or any like aromatic or heterocyclic tertiary amine compound.

The reactions illustrated by the general scheme given above are neither temperature nor pressure sensitive and can be conducted over a broad temperature and pressure range to yield the desired product. Preferably, these reactions are conducted at a temperature of from $-40°$ C. to about $120°$ C. and at atmospheric or autogeneous pressure.

The acid halide, acid, and acid anhydride compounds utilized as reactants in the above reaction scheme are known classes of compounds that can either be obtained from commercial sources or prepared in accordance with conventional methods known to those skilled in the art.

The 2-aryl-1,3-cyclopentanediones utilized as reactants in the above synthetic scheme can be conveniently prepared in accordance with a number of synthetic procedures.

For example, the 2-aryl-1,3-cyclopentanediones may be prepared by the base-promoted cyclization of the appropriate δ-aryl levulinic acid ester. This is illustrated by reacting ethyl-5-(2',4'-dichlorophenyl)-4-ketopentanoate with sodium ethoxide in the presence of a toluene solvent to form 2-(2',4'-dichlorophenyl)-1,3-cyclopentanedione. The δ-aryl levulinic acid esters used as reactants in the above synthesis can be prepared using conventional esterification techniques of the appropriate δ-aryl levulinic acids. δ-aryl levulinic acids can be prepared by the condensation of benzyl cyanides with succinate esters followed by hydrolysis and decarboxylation of the intermediate δ-cyano-δ-aryl levulinate esters.

The 2-aryl-4,5,6,7,8,9-hexahydro-1,3-indandiones are prepared by the base promoted isomerization of the appropriate δ-benzylidene lactone. This is illustrated by reacting 4, 5, 6, 7, 8, 9-hexahydro-3-(2'-methylphenyl)-methylene lactone with sodium ethoxide in the presence of a toluene solvent to form 2-(2'-methylphenyl)-4,5,6,7,8,9-hexahydro-1,3-indandione. The δ-benzylidene lactone can be formed by the acid catalyzed lactonization of the corresponding δ-aryl levulinic acid, a synthesis method known to those skilled in the art.

Preferably, those 2-aryl-1,3-cyclopentanedione compounds, wherein (1) there is a fused ring on the cyclopentane moiety and (2) the 2-phenyl substituent is itself substituted with halogens, may be formed by pinacol rearrangement as outlined in the Journal of The American Chemical Society, (99:3) Feb. 2, 1977, pages 961–962. These synthetic procedures are described in more detail in my copending U.S. patent application Ser. No. 944,995, Entitled "Biocidal 2-Aryl-1,3-Cyclopentanedione Compounds and Alkali Metal and Ammonium Salts Thereof", filed concurrently herewith.

The following acaricidal and herbicidal compounds are illustrative of the compounds of the instant invention:

3-acetoxy-2-(2'-methylphenyl)-2-cyclopentenone 3-(2-ethylhexanoyloxy)-2-(2'-4'-dimethylphenyl)-2-cyclopentenone 3-stearoyloxy-2-(2',4'-dichlorophenyl)-2-cyclopentenone 3-benzoyloxy-2-(2'-methyl-4'-methoxyphenyl)-2-cyclopentenone 3-pivaloyloxy-2-(2'-chloro-5'-methylsulfinylphenyl)-2-cyclopentenone 3-(7-phenylheptanoyloxy)-2-(2'-trifluoromethylphenyl)-2-cyclopentenone 3-(6-chlorohexanoyloxy)-2-(2'-methyl-4'cyanophenyl)-2-cyclopentenone
3-hexanoyloxy-2-(2'-bromo-4'-benzoylphenyl)-2-cyclopentenone
3-(4'-chlorobenzoyloxy)-2-(2'-chloromethyl-4'-acetamidophenyl)-2-cyclopentenone
3-(4'-diethylaminophenylcarbonyloxy)-2-(2',4'-dimethylphenyl)-2-cyclopentenone
3-(4'-methylthiophenylcarbonyloxy)-2-(2'-chlorophenyl)-2-cyclopentenone
3-trifluoroacetoxy-4-ethyl-2-(2',4'-dimethylphenyl-2-cyclopentenone
3-(2-ethylhexanoyloxy)-4,5-diethyl-2-(2',4'-dimethylphenyl)-2-cyclopentenone
3-napthylcarbonyloxy-2-(2',5'-dimethylphenyl)-2-cyclopentenone
3-isobutyryloxy-2-(2'Ochloro-4'-methoxyphenyl)-2-cyclopentenone
3-palmitoyloxy-2-(2'-chloro-4'-methylphenyl)-5-methyl-2-cyclopentenone
3-octanoyloxy-2-(2'-methylphenyl)-5-cyanomethyl-2-cyclopentenone
3-butanoyloxy-2-(2',4'-dimethylphenyl)-5-nitromethyl-2-cyclopentenone
3-methylthioacetoxyl-2-(2',5'-dichlorophenyl)-5-ethyl-2-cyclopentenone
3-cyclopropylcarbonyloxy-2-(2'-methylphenyl)-2-cyclopentenone
3-ethanoyloxy-2-(2'-chlorophenyl)-5-(n-propylsulfinylmethyl)-2-cyclopentenone
3-(4'-methoxyphenylcarbonyloxy)-5-phenylsulfonylmethyl-2-cyclopentenone
3-(2-ethylhexanoyloxy)-2-(2'-fluoro-4'-methylphenyl)-2-cyclopentenone
7-acetoxy-8-(2',4'-dimethylphenyl)bicyclo[4.3.0]non-7-en-9-one
7-(2-ethylhexanoyloxy)-8-(2'-methylphenyl)bicyclo[4.3.0]non-7-en-9-one
7-benzoyloxy-8-(2',4'-dimethylphenyl)-2-methylbicyclo[4.3.0]non-7-en-9-one
7-acetoxy-8-(2',4'-dichlorophenyl)bicyclo[4.3.0]non-7-en-9-one
7-hexanoyloxy-8-(2'-chloro-4'-methylphenyl)bicyclo[4.3.0]non-7-en-9-one
3-acetoxy-2-(2',4'-dimethylphenyl)-4,5,6,7-tetrahydro-2-indenone
3-pivaloyloxy-2-(2',5'-dimethylphenyl)-4,5,6,7-tetrahydro-2-indenone
3-(2-ethylhexanoyloxy)-2-(2'-methylphenyl)-4,5,6,7-tetrahydro-2-indenone
5-acetoxy-4-(2',4'-dimethylphenyl)tricyclo[5.2.1.0$^{2,6}$]dec-4-en-3-one
5-hexanoyloxy-4-(2'-chlorophenyl)tricyclo[5.2.1.0$^{2,6}$]dec-4-en-3-one
3-stearoyloxy-2-(2'-methylphenyl)bicyclo[3.3.0]oct-2-en-1-one
3-benzoyloxy-2-(2',4'-dichlorophenyl)bicyclo[3.2.0]hept-2-en-1-one
3-pentanoyloxy-4,5-dimethyl-2-(2'-methyl-4'-methoxyphenyl)-2-cyclopentenone
3-isobutyryloxy-4-(n-propyl-5-methyl-2-cyclopentenone
3-heptanoyloxy-5-methyl-2-(2'-methyl-4'-cyanophenyl)-2-cyclopentenone
3-acetoxy-2-(2',4'-dimethylphenyl)spiro[4.5]dec-2-en-1-one
3-(2-ethylhexanoyloxy)-2-(2'-chloro-4'-methoxyphenyl)spiro[4.4]non-2-en-1-one
3-decanoyloxy-2-(2',5'-dimethylphenyl)bicyclo[3.3.0]octa-2,4-dienone
3-octanoyloxy-2-(2'-chloro-4'-methylphenyl)bicyclo[3.2.0]hept-2-en-1-one The following specific examples are presented to more particularly illustrate the novel process of this invention and its use in preparing the novel compounds of this invention. The nomenclature used in naming these compounds is illustrated below:

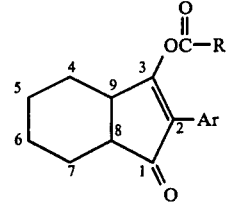

wherein the bonding sites are numbered as shown above.

It should be noted that the instant compounds are considerably more soluble in typical organic solvents, such as those specified above, than are the 2-aryl-1,3-indanedione enol esters of the prior art, making the present compounds readily amenable to formulation as emulsifiable concentrates (E.C.). Unlike the 2-aryl-1,3-indanedione enol esters which are brilliant yellow in color, the present compounds are essentially colorless solids or oils.

EXAMPLE I

Preparation of 3-(2-Ethylhexanoyloxy)-2-(2'-methylphenyl)-4,5,6,7,8,9-hexahydro-2-indenone 3-(2-Ethylhexanoyloxy)-2-(2'-methylphenyl)-4,5,6,7,8,9-hexahydro-2-indenone was prepared from 2-(2'methylphenyl)-4,5,6,7,8,9-hexahydro-1,3-indandione and 2-ethylhexanoyl chloride using the method described above. Part A describes the preparation 2-(2'-methylphenyl)-4,5,6,7,8,9-hexahydro-1,3-indandione from 4,5,6,7,8,9-hexahydro-3-(2'-methylphenyl)methylene lactone.

Part A: Preparation of 2-(2'-methylphenyl)-4,5,6,7,8,9-hexahydro-1,3-indandione

A 500 ml R. B. flask was equipped with a mechanical stirrer, Dean-Stark trap, reflux condenser with N$_2$ inlet, and addition funnel. All of the glassware was dried thoroughly. The flask was charged with 150 ml of dry ethanol and 6.57 g (0.286 mol) of sodium added. The reaction mixture was heated sufficiently to dissolve the sodium. When the sodium had all dissolved, the ethanol was removed by distillation into the Dean-Stark trap. Toluene (150 ml) was added to the residual, powdery sodium ethoxide, and solvent was distilled off until the vapor temperature was 100° C. (Toluene was added slowly during this distillation to maintain the solvent level at 150 ml). Added dropwise to the mixture at 65° C. was 34.61 g (0.143 mol) of 4,5,6,7,8,9-hexahydro-3-(2'-methylphenyl)methylene lactone dissolved in 75 ml of toluene. After the addition was complete, solvent was distilled off until the vapor temperature reached 110° C. (Again toluene was added as necessary to maintain the solvent level at 150 ml). The reaction mixture was cooled to room temperature, surrounded by an ice bath, and 150 ml of ice water added. The aqueous layer was separated from the toluene, and the toluene washed twice with water. The combined basic water layers were extracted twice with ether, then acidified. A tacky tan solid formed which was taken up in 500 ml of methylene chloride, washed 3 times with water, dried (MgSO$_4$), and stripped to leave a tan solid. This solid was triturated with boiling isopropyl ether and the resulting white powdery precipitate filtered off and dried at 75° C. in a vacuum oven. The product, 22.38 g (5% yield), was a white solid, m.p. 139°–142° C.

Part B: Preparation of
3-(2-Ethylhexanoyloxy)-2-(2'-methylphenyl)-4,5,6,7,8,9-hexahydro-2-indenone A suspension of 2.00 g (8.25 mmol) of 2-(2'-methylphenyl)-4,5,6,7,8,9-hexahydro-1,3-indandione in 25 ml of methylene chloride was stirred under N$_2$ and 1.67 g (16.50 mmol) of triethylamine added. To this reaction mixture was added, dropwise, 1.07 g (6.60 mmol) of 2-ethylhexanoyl chloride. The reaction mixture was stirred at room temperature for one hour, and then refluxed for one hour. The solvents were removed on the Rotary Evaporator and the residue shaken with ether and filtered to remove the triethylamine hydrochloride. The ether filtrate was washed twice with water, twice with 0.25N sodium hydroxide, once with 1N HCl, and twice with water. The ether was dried (MgSO$_4$) and removed to leave 2.27 g (93% yield) of the desired product as a clear, colorless oil.

Calcd. for C$_{24}$H$_{32}$O$_3$: C, 78.22; H, 8.75. Found: C, 77.75; H, 8.92.

EXAMPLE II

Preparation of
3-(2-ethylhexanoyloxy)-2-(2',4'-dimethylphenyl)-2-cyclopentenone

A suspension of 2.00 g (9.89 m mol) of 2-(2',4'-dimethylphenyl)-1,3-cyclopentanedione in 25 ml of methylene chloride was stirred under N$_2$ and 2.00 g (19.78 m mol) of triethylamine added. The dione dissolved, and 1.28 g (7.91 m mol) of 2-ethylhexanoyl chloride was added, dropwise. The reaction mixture was stirred at room temperature for one hour and then refluxed for one hour. The solvents were removed on the rotary evaporator and the residue shaken with ether and filtered to remove the triethylamine hydrochloride. The ether filtrate was washed twice with water, twice with 0.25N sodium hydroxide, once with 1N HCl, and twice with water. The ether was dried (MgSO$_4$) and removed to leave 2.52 g (97% yield) of the desired enol ester as a clear, colorless oil.

Calcd. for C$_{21}$H$_{28}$O$_3$: C, 76.79; H, 8.59. Found: C, 76.96; H, 8.55.

EXAMPLE III

Preparation of
3-(2-ethylhexanoyloxy)-2-(2',4'-dimethylphenyl)-4,5,6,7,8,9-hexahydro-2-indenone Using the procedure described in Example II above and starting with 4.62 g (0.0180 mol) of 2-(2',4'-dimethylphenyl)-4,5,6,7,8,9-hexahydro-1,3-indandione, 2.34 g (0.0144 mol) of 2-ethylhexanoyl chloride, and 3.64 g (0.036 mol) of triethylamine, 5.05 g (92% yield) of a light yellow oil was obtained as the desired product.

Calcd. for C$_{25}$H$_{34}$O$_3$: C, 78.49; H, 8.96. Found: C, 78.66; H, 8.97.

EXAMPLE IV

Preparation of
3-(2-ethylhexanoyloxy)-2-(2',5'-dimethylphenyl)-4,5,6,7,8,9-hexahydro-2-indenone Using the procedure described in Example II and starting with 2.00 g (7.80 m mol) of 2-(2',5'-dimethylphenyl)-4,5,6,7,8,9-hexahydro-1,3-indandione, 1.01 g (6.24 m mol) of 2-ethylhexanoyl chloride, and 1.57 g (15.60 m mol) of triethylamine, 2.17 g (91% yield) of a light yellow oil was obtained as the desired product.

Calcd. for C$_{25}$H$_{34}$O$_4$: C, 78.49; H, 8.96. Found: C, 78.66; H, 8.97.

EXAMPLE V

Preparation of
3-acetoxy-2-(2'-methylphenyl)-4,5,6,7,8,9-hexahydro-2-indenone

A mixture of 2.00 g (8.25 m mol) of 2-(2'-methylphenyl)-4,5,6,7,8,9-hexahydro-1,3-indandione, 1.68 g (16.50 m mol) of acetic anhydride, and 25 ml. of pyridine was stirred overnight at room temperature. The reaction mixture was then poured into water and extracted three times with ether. The ether was washed with 100 ml of ice-cold 50% HCl, water, 1N sodium hydroxide, and water again. The ether was dried (MgSO$_4$) and the ether removed under reduced pressure to yield 1.96 g (84% yield) of the desired enol acetate as a yellow oil.

Calcd. for C$_{18}$H$_{20}$O$_3$: C, 76.03; H, 7.09. Found: C, 75.77; H, 6.96.

EXAMPLE VI

Preparation of
3-benzoyloxy-2-(2',4'-dimethylphenyl)-4,5,6,7,8,9-hexahydro-2-indenone Using the procedure described in Example II and starting with 4.62 g (0.0180 mol) of 2-(2',4'-dimethylphenyl)-4,5,6,7,8,9-hexahydro-1,3-indandione, 2.02 g (0.0144 mol) of benzoyl chloride, and 3.64 g (0.0360 mol) of triethylamine, 5.28 g (95% yield) of a light yellow oil was obtained as the desired product.

Calcd. for C$_{24}$H$_{24}$O$_3$: C, 79.97; H, 6.71. Found: C, 79.58; H, 6.75.

The remainder of the compounds in Table I were prepared in a manner similar to that illustrated in the above examples and are listed with an elemental analysis.

Selected 2-aryl-1,3-cyclopentanedione enol ester compounds, representative of those useful in accordance with this invention were tested with respect to their miticidal, mite ovicidal and pre-emergent and post-emergent herbicidal activity. It was found that the compounds of the instant invention exhibited improved pesticidal activity, particularly miticidal activity, over structurally similar prior art compounds.

Suspensions of the test compounds were prepared by dissolving one gram of compound in 50 milliliters of acetone in which had been dissolved 0.1 gram (10 percent of the weight of compound) of an alkylphenoxyethanol sufactant, as an emulsifying or dispersing agent. The resulting solution was mixed into 160 milliliters of water to give roughly 200 milliliters of a suspension containing the compound in finely divided form. The thus prepared stock suspension contained 0.5 percent by weight of compound. The test concentrations employed in the tests described below were obtained by diluting the stock suspension with water. The test procedures were as follows:

MITE FOLIAGE SPRAY TEST

Adults and nymphal stages of the two-spotted mite (*Tetranychus urticae* (Koch)), reared in Tendergreen bean plants at 80°±5° F. and 50±5 percent relative humidity, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty-four hours. Following the twenty-four hour transfer period, the excised leaves were removed from the infested plants. The test compounds were formulated by diluting the stock suspension with water to provide suspensions containing the desired amount of test compound per million parts of final formulation. The potted plants (one pot per compound) were placed on a revolving turntable and sprayed with 100-110 milliliters of test compound formulation by use of a DeVilbis spray gun set at 40 psi. air pressure. This application, which lasted 30 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80°±5° F. and 50±5 percent relative humidity for four days, after which, a mortality count of motile forms was made on the leaves of the test plants. Any individual which was capable of locomotion upon prodding was considered living.

MITE OVICIDE TEST

The test organism was the egg of the two-spotted mite (*Tetranychus urticae* (Koch)), as obtained from adults reared on Tendergreen bean plants under controlled conditions of 80°±5° F. and 50±5 percent relative humidity. Heavily infested leaves from a stock culture were placed on the primary leaves of two bean plants six to eight inches in height growing in a two-and-a-half inch clay pot. Females were allowed to oviposit for a period of 48 hours and then the leaves of the infested plants were dipped in a solution containing 800 parts of tetraethyl pyrophosphate per million parts of water in order to destroy the reproductory forms and thus prevent further egg laying. This solution of tetraethyl pyrophosphate does not affect the viability of the eggs. The plants were allowed to dry thoroughly. The test compounds were formulated by diluting the stock suspension with water to give a suspension containing varying amounts of test compound per million parts of final formulation. The potted plants (one pot per compound) were placed on a revolving turntable and sprayed with 100-110 milliliters of test compound formulation by use of a DeVilbis sray gun set at 40 spig. air pressure. This application which lasted 30 seconds, was sufficient to wet the plants to run-off. As a control, 100-110 milliliters of a water solution containing acetone and emulsifier in the same concentrations as the test compound formulation, but containing no test compound, were also sprayed on plants infested with eggs. The sprayed plants were held at 80°±5° F. and 50±5 percent relative humidity for four days, after which a microscopic examination was made of unhatched (dead) and hatched (living) eggs.

In these tests the pesticidal activity of the compounds against mites and mite eggs was rated as follows:
A=Excellent Control
B=Partial Control
C=No Control

PRELIMINARY HERBICIDE SEED GERMINATION TEST

The following seeds were used in this test:
Perennial rye grass—*Solium perenne*
Crabgrass—*Digitaria sanguinalis*
Red root pigweed—*Amaranthus retroflexus*
Mustard—*Brassica pincea var. foliosa* (Florida broadleaf)
Two seed-oil mixtures were prepared as follows:
Mixture I
  196 cc. Rye grass seed
  75 cc. Mustard seed
  18,000 cc. Sifted, fairly dry soil
Mixture II
  99 cc. Crabgrass seed
  33 cc. Amaranthus
  18,000 cc. Sifted, fairly dry soil Each of the above mixtures was rolled separately in 5 gallon containers for approximately one-half hour on ball mill to insure uniform mixing of seeds and soil. For each compound four 3-inch pots were filled with soil to within 1½ inches of top of pots. To two of these pots were added 70 cc. of Mixture I. To the remaining 2 pots were added 70 cc. of Mixture II. The seed-soil mixture was tamped firmly, and the pots were removed to the greenhouse and watered lightly. About 2 hours after planting, 25 milliliters of the test formulation were added to one pot containing Mixture I and one pot containing Mixture II. An equal volume of a water solution containing acetone and an emulsifier in the same concentration as the herbicidal mixture but without the candidate herbicide was also added to each of the soil-seed mixtures. These pots are used as check or control units. The test compounds were formulated by diluting the stock suspension with water to obtain the desired concentration of the compound in parts per million of the final formulation. Each compound was tested at the same concentration. Ten to twelve days after application of the chemical, injury was noted for each species by comparing treated versus untreated pots. Ratings were made according to the following designations:
5=no seedling emerged
4=few seedlings emerged and/or very severe stunting
3=moderate reduction in stand and/or moderate stunting.
2=very slight reduction in stand and/or slight stunting
1=no injury, seedlings appear no different with respect to stand or growth than untreated controls

POST-EMERGENT HERBICIDAL TEST

Experiments were also conducted to determine the phytotoxicity of representative compositions with respect to healthy fresh plants. Solutions of the compounds were prepared as described above to provide a concentration of 2500 parts per million of the test compound. The test plants were sprayed in accordance with the procedure described above for the Mite Foliage Spray Test so as to deliver approximately 100 milliliters of test solutions to the leaves of each plant tested. The sprayed plants and controls were set aside for approximately one hour to allow the solutions to dry and were then placed in the greenhouse. After ten days the plants were visually inspected to determine the extent of foliage injury. A rating of 1 indicates no perceptible injury; 5 indicates the plant was dead and ratings of 2, 3 and 4 indicate intermediate degrees of injury based upon the number and extent to which leaves were injured.

The results of these experiments are summarized and set forth in Table II below.

TABLE I

Elemental Analysis of 2-Aryl-1,3 CYCLOPENTANEDIONE ENOL ESTER COMPOUNDS

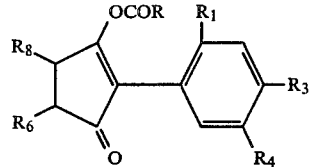

| Compound # | $R_1$ | $R_3$ | $R_4$ | $R_6$ | $R_8$ | R | Molecular Formula | Calculated C | Calculated H | Found C | Found H |
|---|---|---|---|---|---|---|---|---|---|---|---|
| 1 | Cl | H | H | H | H | $CH_2CH_3$ $-CH(CH_2)_3CH_3$ | | 68.15 | 6.92 | 68.82 | 6.83 |
| 2 | Cl | H | H | H | H | $-C_6H_5$ | | 69.12 | 4.19 | 68.94 | 3.98 |
| 3 | Cl | Cl | H | H | H | $-CH_3$ | | 54.76 | 3.53 | 55.09 | 3.35 |
| 4 | Cl | Cl | H | H | H | $-CH(CH_3)_2$ | | 57.52 | 4.51 | 57.91 | 4.23 |
| 5 | Cl | Cl | H | H | H | $CH_2CH_3$ $-CH(CH_2)_3CH_3$ | | 61.80 | 6.00 | 62.26 | 6.13 |
| 6 | Cl | Cl | H | H | H | $-(CH_2)_{14}CH_3$ | | 67.35 | 7.96 | 67.46 | 8.08 |
| 7 | $CH_3$ | H | H | H | H | $CH_2CH_3$ $-CH(CH_2)_3CH_3$ | | 76.40 | 8.34 | 76.26 | 8.33 |
| 8 | $CH_3$ | H | H | H | H | $-(CH_2)_{14}CH_3$ | | 78.82 | 9.92 | 78.96 | 9.93 |
| 9 | $CH_3$ | $CH_3$ | H | H | H | $CH_2CH_3$ $-CH(CH_2)_3CH_3$ | | 76.79 | 8.59 | 76.96 | 8.55 |
| 10 | $CH_3$ | $CH_3$ | H | H | H | $-C_6H_5$ | | 78.41 | 5.92 | 77.26 | 5.74 |
| 11 | $CH_3$ | H | $CH_3$ | H | H | $-CH_3$ | | 73.75 | 6.60 | 73.52 | 6.41 |
| 12 | $CH_3$ | H | $CH_3$ | H | H | $-CH(CH_3)_2$ | | 74.97 | 7.40 | 75.08 | 7.22 |
| 13 | $CH_3$ | H | $CH_3$ | H | H | $CH_2CH_3$ $-CH(CH_2)_3CH_3$ | | 76.79 | 8.60 | 76.95 | 8.49 |
| 14 | $CH_3$ | H | $CH_3$ | H | H | $-(CH_2)_{14}CH_3$ | | 79.04 | 10.06 | 79.39 | 10.04 |
| 15 | $CH_3$ | H | $CH_3$ | $CH_3$ | H | $-CH_3$ | | 74.40 | 7.02 | 74.82 | 7.03 |
| 16 | $CH_3$ | H | $CH_3$ | $CH_3$ | H | $-CH(CH_3)_2$ | | 75.50 | 7.74 | 76.21 | 7.86 |
| 17 | $CH_3$ | H | $CH_3$ | $CH_3$ | H | $CH_2CH_3$ $-CH(CH_2)_3CH_3$ | | 77.15 | 8.83 | 77.79 | 8.84 |
| 18 | $CH_3$ | H | $CH_3$ | $CH_3$ | H | $-(CH_2)_{14}CH_3$ | | 79.24 | 10.20 | 79.73 | 10.15 |
| 19 | $CH_3$ | H | H | $-(CH_2)_4-$ | | $-CH_3$ | | 76.03 | 7.09 | 75.77 | 6.96 |
| 20 | $CH_3$ | H | H | $-(CH_2)_4-$ | | $-CH(CH_3)_2$ | $C_{20}H_{24}O_3$ | 76.89 | 7.74 | 76.81 | 7.54 |
| 21 | $CH_3$ | H | H | $-(CH_2)_4-$ | | $CH_2CH_3$ $-CH(CH_2)_3CH_3$ | $C_{24}H_{32}O_3$ | 78.22 | 8.75 | 77.75 | 8.92 |
| 22 | $CH_3$ | H | H | $-(CH_2)_4-$ | | $-C(CH_3)_3$ | $C_{21}H_{26}O_3$ | 77.27 | 8.03 | 77.24 | 7.83 |
| 23 | $CH_3$ | H | H | $-(CH_2)_4-$ | | $-(CH_2)_8CH_3$ | $C_{26}H_{36}O_3$ | 78.74 | 9.15 | 78.34 | 9.08 |
| 24 | $CH_3$ | H | H | $-(CH_2)_4-$ | | $-(CH_2)_{14}CH_3$ | $C_{32}H_{48}O_3$ | 79.95 | 10.07 | 80.34 | 10.33 |
| 25 | $CH_3$ | $CH_3$ | H | $-(CH_2)_4-$ | | $-CH_3$ | $C_{19}H_{22}O_3$ | 76.48 | 7.43 | 76.40 | 7.38 |
| 26 | $CH_3$ | $CH_3$ | H | $-(CH_2)_4-$ | | $CH_2CH_3$ $-CH(CH_2)_3CH_3$ | $C_{25}H_{34}O_3$ | 78.49 | 8.96 | 78.66 | 8.97 |
| 27 | $CH_3$ | $CH_3$ | H | $-(CH_2)_4-$ | | $-C_6H_5$ | $C_{12}H_{24}O_3$ | 79.97 | 6.71 | 79.58 | 6.75 |
| 28 | $CH_3$ | H | $CH_3$ | $-(CH_2)_4-$ | | $-CH_3$ | $C_{19}H_{22}O_3$ | 76.48 | 7.44 | 76.58 | 7.20 |
| 29 | $CH_3$ | H | $CH_3$ | $-(CH_2)_4-$ | | $-CH(CH_3)_2$ | $C_{21}H_{26}O_3$ | 77.26 | 8.03 | 77.50 | 7.64 |

TABLE I-continued

Elemental Analysis of 2-Aryl-1,3 CYCLOPENTANEDIONE ENOL ESTER COMPOUNDS

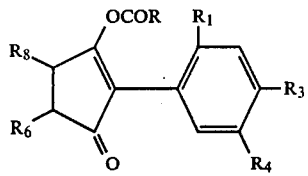

| Compound # | $R_1$ | $R_3$ | $R_4$ | $R_6$ | $R_8$ | R | Molecular Formula | Calculated C | Calculated H | Found C | Found H |
|---|---|---|---|---|---|---|---|---|---|---|---|
| 30 | $CH_3$ | H | $CH_3$ | $-(CH_2)_4-$ | | $CH_2CH_3$<br>\|<br>$-CH(CH_2)_3CH_3$ | $C_{25}H_{34}O_3$ | 78.49 | 8.96 | 78.72 | 8.96 |
| 31 | $CH_3$ | H | $CH_3$ | $-(CH_2)_4-$ | | $-C(CH_3)_3$ | $C_{22}H_{28}O_3$ | 77.61 | 8.29 | 77.95 | 8.22 |
| 32 | $CH_3$ | H | $CH_3$ | $-(CH_2)_4-$ | | $-(CH_2)_8CH_3$ | $C_{27}H_{38}O_3$ | 79.98 | 9.33 | 79.07 | 9.25 |
| 33 | $CH_3$ | H | $CH_3$ | $-(CH_2)_4-$ | | $-(CH_2)_{14}CH_3$ | $C_{33}H_{50}O_3$ | 80.11 | 10.19 | 80.39 | 10.26 |

TABLE II

Biocidal Activity of 2-Aryl-1,3-Cyclopentanedione Enol Ester Compounds

| Compound No. | Miticidal Adult | Miticidal Egg | Post-emergent Herbicidal Bean | Corn | Tomato | Cotton | Soybean | Pre-emergent Herbicidal Rye | Crabgrass | Amaranthus | Mustard |
|---|---|---|---|---|---|---|---|---|---|---|---|
| 1 | A | A | 3 | 4 | 2 | 3 | 3 | 5 | 5 | 5 | 5 |
| 2 | A | A | 3 | 3 | 2 | 2 | 2 | 4 | 3 | 1 | 1 |
| 3 | A | A | 2 | 3 | 2 | 2 | 2 | 2 | — | 2 | 1 |
| 4 | B | B | 2 | 4 | 2 | 2 | 2 | 1 | — | 1 | 1 |
| 5 | A | A | 3 | 3 | 2 | 2 | 2 | 1 | — | 1 | 1 |
| 6 | A | B | 1 | 1 | 1 | 1 | 1 | 1 | — | 1 | 1 |
| 7 | A | A | 2 | 2 | 2 | 2 | 2 | 5 | 3 | 3 | 1 |
| 8 | A | B | 3 | 3 | 1 | 2 | 3 | 2 | 2 | 3 | 1 |
| 9 | A | A | 2 | 3 | 1 | 1 | 1 | 5 | 4 | 2 | 2 |
| 10 | C | B | 3 | 3 | 1 | 1 | 1 | 3 | 2 | 1 | 1 |
| 11 | A | C | 2 | 2 | 3 | 2 | 2 | 4 | 1 | 3 | 3 |
| 12 | B | B | 2 | 2 | 3 | 3 | 3 | 1 | 1 | 1 | 1 |
| 13 | A | A | 2 | 2 | 2 | 3 | 3 | 1 | 1 | 1 | 1 |
| 14 | A | A | 2 | 1 | 3 | 3 | 3 | 4 | 1 | 1 | 1 |
| 15 | A | B | 2 | 3 | 2 | 2 | 2 | 4 | 2 | 3 | 2 |
| 16 | B | B | 3 | 3 | 2 | 3 | 2 | 3 | 1 | 3 | 2 |
| 17 | A | A | 3 | 3 | 1 | 3 | 3 | 3 | 1 | 3 | 1 |
| 18 | A | A | 2 | 3 | 2 | 2 | 2 | 4 | 1 | 1 | 1 |
| 19 | A | A | 3 | 5 | 2 | 2 | 3 | 3 | 3 | 4 | 3 |
| 20 | A | A | 3 | 5 | 1 | 3 | 3 | 4 | 3 | 3 | 3 |
| 21 | A | A | 1 | 5 | 1 | 2 | 2 | 3 | 2 | 2 | 1 |
| 22 | A | A | 2 | 5 | 1 | 3 | 3 | 5 | 3 | 2 | 3 |
| 23 | A | A | 2 | 5 | 1 | 3 | 3 | 5 | 3 | 3 | 3 |
| 24 | A | A | 1 | 2 | 1 | 2 | 2 | 4 | 3 | 2 | 3 |
| 25 | A | A | 1 | 3 | 2 | 3 | 2 | 5 | 5 | 3 | 3 |
| 26 | A | A | 2 | 5 | 2 | 2 | 2 | 5 | 1 | 1 | 1 |
| 27 | A | A | 1 | 4 | 2 | 2 | 2 | 5 | 5 | 4 | 5 |
| 28 | A | A | 2 | 3 | 1 | 1 | 2 | 3 | 2 | 1 | 1 |
| 29 | A | A | 1 | 2 | 1 | 2 | 2 | 1 | 1 | 1 | 1 |
| 30 | A | A | 1 | 2 | 1 | 1 | 1 | 1 | 1 | 1 | 1 |
| 31 | A | A | 1 | 2 | 1 | 1 | 2 | 1 | 1 | 1 | 1 |
| 32 | A | A | 1 | 2 | 1 | 1 | 1 | 1 | 1 | 1 | 1 |
| 33 | A | A | 1 | 1 | 1 | 1 | 1 | 1 | 1 | 1 | 1 |

Additional experimental work was conducted in order to compare compounds of the present invention with 2-aryl-1,3-indandione enol esters of the prior art. Two references, U.S. Pat. No. 4,104,043 (Reference I) and Durden, Jr., "Biocidal Activity of Indanediones, et J. Med. Chem. IV, pp. 143-71 (1974) (Reference II) were used as illustrative of the prior art.

Tests were conducted in accordance with the procedures given at pages 17 to 21 supra. The results are expressed in the same manner as used in Table II, except with respect to miticidal activity. For mite adult and mite egg comparison purposes, results are given in parts per million (ppm) required for a 50 percent kill of mites or eggs, respectively.

The results are given in Table III which follows:

TABLE III

COMPARISON OF MITICIDAL POST-EMERGENT, AND PRE-EMERGENT HERBICIDAL ACTIVITY OF INSTANT COMPOUNDS WITH 2-ARYL-1,3-INDANDIONE ENOL ESTERS.

| Reference | Compound | Miticidal $LD_{50}$, PPM Adult | Egg | Post Emergent Herbicidal Bean | Corn | Tomato | Cotton | Soybean | Pre-Emergent Herbicidal Rye | Crabgrass | Amaranthus | Mustard |
|---|---|---|---|---|---|---|---|---|---|---|---|---|
| Present Invention | [2-(2-methylphenyl)-4,5,6,7-tetrahydroindanone enol nonanoate] | 2 | 1 | 2 | 5 | 1 | 3 | 3 | 5 | 3 | 3 | 3 |
| Generically Encompassed by Reference I | [2-(2-methylphenyl)-1,3-indandione enol nonanoate] | 500 | 500 | 1 | 1 | 1 | 1 | 0 | 1 | 1 | 1 | 1 |
| Present Invention | [2-(2-methylphenyl)-4,5,6,7-tetrahydroindanone enol pentadecanoate] | 20 | 500 | 1 | 2 | 1 | 2 | 2 | 4 | 3 | 2 | 3 |
| Reference II, p. 155, compound 60. | [2-(2-methylphenyl)-1,3-indandione enol pentadecanoate] | 500 | 60 | 1 | 1 | 1 | 1 | 0 | 1 | 1 | 1 | 1 |
| Present Invention | [2-(2,5-dimethylphenyl)-4,5,6,7-tetrahydroindanone enol nonanoate] | 25 | 8 | 1 | 2 | 1 | 1 | 1 | 1 | 1 | 1 | 1 |
| Generically Encompassed by Reference I | [2-(2,5-dimethylphenyl)-1,3-indandione enol nonanoate] | 500 | 500 | 1 | 1 | 1 | 1 | 0 | 1 | 1 | 1 | 1 |
| Present Invention | [2-(2-methylphenyl)-cyclopentenone enol 2-ethylhexanoate] | 220 | 125 | 2 | 2 | 2 | 2 | 2 | 5 | 3 | 3 | 1 |
| Present Invention | [2-(2-methylphenyl)-4,5,6,7-tetrahydroindanone enol 2-ethylhexanoate] | 7 | 5 | 1 | 5 | 1 | 2 | 2 | 3 | 2 | 2 | 1 |

TABLE III-continued
COMPARISON OF MITICIDAL POST-EMERGENT, AND PRE-EMERGENT HERBICIDAL ACTIVITY OF INSTANT COMPOUNDS WITH 2-ARYL-1,3-INDANDIONE ENOL ESTERS.

| Reference | Compound | Miticidal $LD_{50}$, PPM Adult | Egg | Post Emergent Herbicidal Bean | Corn | Tomato | Cotton | Soybean | Pre-Emergent Herbicidal Rye | Crabgrass | Amaranthus | Mustard |
|---|---|---|---|---|---|---|---|---|---|---|---|---|
| Generically encompassed by Refernce I | [structure: indanone with O=C-CH(CH₂)₃CH₃ / CH₂CH₃ enol ester, 2-(o-methylphenyl)] | 500 | 60 | 1 | 1 | 1 | 1 | 0 | 1 | 1 | 1 | 1 |
| Present Invention | [structure: hexahydroindanone with O-C(=O)-C(CH₃)₃ enol ester, 2-(o-methylphenyl)] | 15 | 16 | 2 | 5 | 1 | 3 | 3 | 5 | 3 | 2 | 3 |
| Reference II, page 155, compound 59 | [structure: indanone with O-C(=O)-C(CH₃)₃ enol ester, 2-(o-methylphenyl)] | 100 | 270 | 1 | 1 | 1 | 1 | 0 | 2 | 2 | 2 | 2 |

It will be understood that the plant species employed in the above tests are merely representative of a wide variety of plant pest that can be controlled by the use of the compounds of this invention. The compounds contemplated in this invention may be applied as acaricides, pre-emergent and post-emergent herbicides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric or cationic dispersing and emulsifying agents may be employed, for example, the condensation products of alkylene oxides with phenol and organic acids, alkyl aryl sulfonates complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by acarids, particularly mites, upon plants or other material to which the pesticides are applied, and they have relatively high residual toxicity. With respect to plants, they are relatively safe to plants when used in sufficient amount to kill or repel the acarids or other plant pests, and they resist weathering which includes wash-off caused by rain, decomposition by ultraviolet light, oxidation, or hydrolysis in the presence of moisture or, at least such decomposition, oxidation, and hydrolysis as would materially decrease the desirable pesticidal characteristic of the toxicants. The toxicants are so chemically inert that they are compatible with substantially any other constituents of the spray schedule. Mixtures of the active compounds may be employed if desired as well as combinations of the active compounds of this invention with other biologically active compounds.

What is claimed is:

1. An acaricidal or herbicidal composition comprising an acceptable carrier and as the active toxicant an acaricidally or herbicidally effective amount of a compound of the formula:

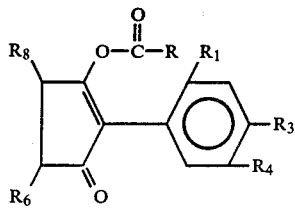

wherein:

R is $C_1$–$C_{15}$ linear alkyl, $C_1$–$C_{15}$ branched alkyl or phenyl;

$R_1$ is alkyl or halogen;

$R_3$ and $R_4$ are individually hydrogen, alkyl or halogen;

$R_6$ is hydrogen, alkyl or alkylene; and $R_8$ is hydrogen or $R_6$ and $R_8$ together form a six-membered alkylene ring.

2. A composition according to claim 1 wherein:

$R_1$ is methyl or halogen;

$R_3$ and $R_4$ are individually hydrogen, methyl or halogen;

$R_6$ is methyl; and $R_8$ is hydrogen or $R_6$ and $R_8$ together form a six-membered alkylene ring.

3. An acaricidal or herbicidal composition comprising an acceptable carrier and as the active toxicant an acaricidally or herbicidally effective amount of a compound of the formula:

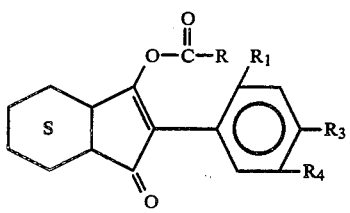

wherein:

R is $C_1$–$C_{15}$ linear alkyl, $C_1$–$C_{15}$ branched alkyl or phenyl;

$R_1$ is alkyl or halogen; and $R_3$ and $R_4$ are individually hydrogen, alkyl or halogen.

4. A method of controlling acarids or plant pests which comprises subjecting the acarids or the plant pests to an acaricidally or herbicidally effective amount of a compound of the formula:

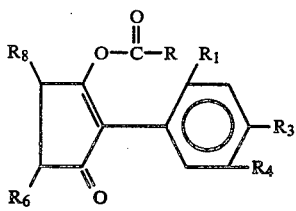

wherein:

R is $C_1$–$C_{15}$ linear alkyl, $C_1$–$C_{15}$ branched alkyl or phenyl;

$R_1$ is alkyl or halogen;

$R_3$ and $R_4$ are individually hydrogen, alkyl or halogen;

$R_6$ is hydrogen, alkyl or alkylene; and $R_8$ is hydrogen or $R_6$ and $R_8$ together form a six-membered alkylene ring.

5. A method according to claim 4 wherein:

$R_1$ is methyl or halogen;

$R_3$ and $R_4$ are individually hydrogen, methyl or halogen;

$R_6$ is methyl; and $R_8$ is hydrogen or $R_6$ and $R_8$ together form a six-membered alkylene ring.

6. A method of controlling acarids or plant pests which comprises subjecting the acarids or the plant pests to an acaricidally or herbicidally effective amount of a compound of the formula:

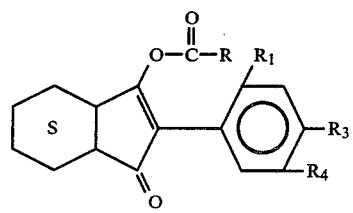

wherein:

R is $C_1$–$C_{15}$ linear alkyl, $C_1$–$C_{15}$ branched alkyl or phenyl;

$R_1$ is alkyl or halogen; and $R_3$ and $R_4$ are individually hydrogen, alkyl or halogen.

7. A composition according to claim 3 wherein:

the active toxicant is 3-(2-ethylhexanoyloxy)-2-(2'-methylphenyl)-4,5,6,7,8,9-hexahydro-2-indenone.

8. A composition according to claim 3 wherein:

the active toxicant is 3-(2-ethylhexanoyloxy)-2-(2'-4'dimethylphenyl)-4,5,6,7,8,9-hexahydro-2-indenone.

9. A composition according to claim 3 wherein:

the active toxicant is 3-(2-Ethylhexanoyloxy)-2-(2',5'-dimethylphenyl)-4,5,6,7,8,9-hexahydro-2-indenone.

10. A compound according to claim 1 wherein:

the active toxicant is 3-(2-Ethylhexanoyloxy)-2-(2',4'-dimethylphenyl)-2-cyclopentenone.

11. The method according to claim 6 wherein:

the compound is 3-(2-Ethylhexanoyloxy)-2-(2'-methylphenyl)-4,5,6,7,8,9-hexahydro-2-indenone.

12. The method according to claim 6 wherein:

the compound is 3-(2-Ethylhexanoyloxy)-2-(2',4'dimethylphenyl)-4,5,6,7,8,9-hexahydro-2-indenone.

13. The method according to claim 6 wherein:

the compound is 3-(2-Ethylhexanoyloxy)-2-(2'5'-dimethylphenyl)-4,5,6,7,8,9-hexahydro-2-indenone.

14. The method according to claim 4 wherein:

the compound is 3-(2-Ethylhexanoyloxy)-2-(2',4'-dimethylphenyl)-2-cyclopentenone.

* * * * *